United States Patent [19]
Abe et al.

[11] Patent Number: 5,902,739
[45] Date of Patent: May 11, 1999

[54] METHOD OF PRODUCING ERYTHRITOL

[75] Inventors: Shuuichi Abe; Satoshi Morioka, both of Yokohama, Japan

[73] Assignee: Mitsubishi Chemical Corporation, Japan

[21] Appl. No.: 08/982,410

[22] Filed: Dec. 2, 1997

[30] Foreign Application Priority Data

Dec. 2, 1996 [JP] Japan .................................. 8-321466

[51] Int. Cl.$^6$ ...................................................... C12P 7/18
[52] U.S. Cl. ........................... 435/158; 435/171; 435/911
[58] Field of Search ..................... 435/158, 911, 435/171

[56] References Cited

U.S. PATENT DOCUMENTS 4,923,812  5/1990  Horikita et al. ....................... 435/158
4,939,091  7/1990  Sasaki et al. ........................... 435/158
5,036,011  7/1991  Sasaki et al. ........................... 514/333

OTHER PUBLICATIONS

Biotech Abstract 93–10502 JP5137585 Mitsubishi Chem "Erythritol Production and Purification", Jun. 1, 1993.

*Primary Examiner*—Herbert J. Lilling
*Attorney, Agent, or Firm*—Wenderoth, Lind & Ponack, L.L.P.

[57] ABSTRACT

In the method of producing erythritol by cultivating a yeast strain capable of producing erythritol from fermentable carbohydrate in a culture medium containing the carbohydrate as a main carbon source to recover erythritol from the culture, erythritol can be produced efficiently in high yield by using ammonium sulfate as a main nitrogen source in the culture medium.

12 Claims, No Drawings

METHOD OF PRODUCING ERYTHRITOL

FIELD OF THE INVENTION

The present invention relates to a method of producing erythritol, more specifically, to a method of producing erythritol by fermentation using ammonium sulfate as a main nitrogen source in a culture medium, which is advantageous to industrial production.

BACKGROUND OF THE INVENTION

Known methods of producing erythritol include a method comprising cultivating a yeast strain belonging to the genus Trigonopsis or Candida in a culture medium containing glycerol as a carbon source and casein hydrolysate as a nitrogen source (Japanese Patent Publication No. 47-41549), and a method comprising cultivating a yeast strain belonging to the genus Candida, Torulopsis, or Hansenula in a culture medium containing hydrocarbons and the like as carbon sources and yeast extract and urea as nitrogen sources (Japanese Patent Publication No. 51-21072). These methods, however, have not yet been industrialized since raw materials used as carbon sources are not suitable for actual industrial production.

Alternatively, it is known to produce erythritol by cultivating *Moniliella tomentosa* var. *pollinis* in a culture medium containing carbohydrate such as glucose as carbon sources and corn steep liquor, urea, and yeast extract as nitrogen sources (Japanese Patent Laid Open No.60-110295 and the like) or by cultivating erythritol-producing microorganism in a culture medium containing yeast extract and corn steep liquor as nitrogen sources (Japanese Patent Laid-Open No. 1-199584).

Various substances are known as nitrogen sources as described above. However, urea is not admitted as food additives and therefore, it cannot be used for the production of erythritol which is applied to foods. On the other hand, yeast extract and casein hydrolysate is very expensive and therefore, they cannot be necessarily advantageous to industrial production. When corn steep liquor is used as a main nitrogen source, glycerol may be produced as a by-product, erythritol produced may be colored brown, or it contains a large quantity of salt. For these reasons, the purification process overloaded, which is disadvantageous to economical production.

SUMMARY OF THE INVENTION

An object of the present invention is to provide a method of producing erythritol suitable for food additive by using safe and inexpensive nitrogen sources.

As a result of intensive investigation to solve the above problems, the present inventors have found that the above object can be achieved by using ammonium sulfate which are admitted as food additives as a main nitrogen source.

The gist of the present invention resides in a method of producing erythritol comprising the steps of cultivating a yeast strain capable of producing erythritol from fermentable carbohydrate in a culture medium containing the fermentable carbohydrate as a carbon source and recovering erythritol from the culture, in which ammonium sulfate is used as a main nitrogen source in the culture medium.

The preferred embodiments to carry out the present invention include: the above method in which, as a nitrogen source in the culture medium, ammonium sulfate is used in an amount of from 50 to 85% of the total nitrogen sources in terms of nitrogen atom; the above method in which, the medium further contains corn steep liquor as a nitrogen source, and an amount of ammonium sulfate ranges from 50 to 85% and an amount of corn steep liquor ranges from 15 to 50%, of the total nitrogen sources in the medium in terms of nitrogen atom; the above method in which the yeast strain belongs to the genus Moniliella; the above method in which the yeast strain is *Moniliella pollinis*; the above method in which the yeast strain belongs to the genus Yarrowia; the above method in which the yeast strain is *Yarrowia lipolytica*; the above method in which the yeast strain belongs to the genus Trichosporonoides; the above method in which the yeast strain is selected from *Trichosporonoides oedocephalis*, *Trichosporonoides nigrescens* and *Trichosporonoides megachiliensis*; the above method in which the fermentable carbohydrate is selected from glucose, fructose and glycerol; the above method in which the nitrogen source is contained in the culture medium in a concentration of 0.1 to 5.0% (w/v); and the above method in which a pH of the culture medium is maintained at 3.0 to 7.0.

DETAILED DESCRIPTION OF THE INVENTION

The present invention will be described in detail below.

Any yeast strain can be used in the present invention as long as it can produce erythritol from fermentable carbohydrate. Specifically, the yeast strain belonging to the genus Moniliella, Yarrowia, Trichosporonoides can be used. More specifically, examples thereof include *Moniliella pollinis* as the strain belonging to the genus Moniliella, *Yarrowia lipolytica* as the strain belonging to the genus Yarrowia, *Trichosporonoides oedocephalis*, *Trichosporonoides nigrescens*, and *Trichosporonoides megachiliensis* as the strain belonging to the genus Trichosporonoides. These strains may be mutants obtained by UV irradiation, N-methyl-N'-nitrosoguanidine (NTG) treatment, ethyl methanesulfonate (EMS) treatment, nitrous acid treatment, acridine treatment, and the like, or recombinant strains genetically produced by means of cell fusion or recombinant DNA techniques.

One or two or more of the above-described strains can be used in the method according to the present invention.

Specific examples of such mutants include *Moniliella pollinis* MCI3371 which is mutant of *Moniliella pollinis* CBS 461.67, *Moniliella pollinis* MCI3555 which is a mutant of *Moniliella pollinis* MCI3554, *Yarrowia lipolytica* ATCC8661, *Trichosporonoides oedocephalis* MCI3440 which is a mutant of *Trichosporonoides oedocephalis* CBS568.85, *Trichosporonoides megachiliensis* MCI3369 which is a mutant of *Trichosporonoides megachiliensis* CBS567.85, and *Trichosporonoides nigrescens* MCI3437 which is a mutant of CBS268.81.

The above strains except for *Yarrowia lipolytica* ATCC8661 are mutants whose yeastiness is reduced by treating the strains which have been deposited at one of the International Depository Authorities, Centraal Bureau voor Schimmelcultures (CBS), Netherlands or the strains isolated from nature by the present inventors with ultraviolet irradiation or with a mutagen such as N-methyl-N'-nitrosoguanidine (NTG) or the like. MCI3369, MCI3371, MCI3437, MCI3440, MCI3554 and MCI3555 have been deposited at National Institute of Bioscience and Human-Technology, Agency of Industrial Science and Technology (postal code: 305, 1–3, Higashi 1-chome, Tsukuba-shi, Ibaraki-ken, Japan), under the deposition numbers of FERM BP-6172, FERM BP-6173, FERM BP-6174, FERM BP-6175, FERM BP-6170 and FERM BP-6171. *Yarrowia*

*lipolytica* ATCC8661 has been deposited at American Type Culture Collection (ATCC), U.S.A. as well as National Institute of Bioscience and Human-Technology, Agency of Industrial Science and Technology, Japan under the deposition number of FERM BP-6169. Mycological properties of MCI3369, MCI3371, MCI3437, MCI3440, MCI3554, and MCI3555 are described below.

MCI3369:

The color of the colony of strain MCI3369 is white initially, then olive-gray, and, after more than two-week culture, olive-dark brown when cultivated at 24° C. on PDA medium. The strain rapidly grows and proliferates by budding like yeasts. The color of the yeast-like cells is colorless initially and then olive-dark brown. Its vegetative hyphae grow well and branch with forming septum. The hyphae have the width ranging from 2 to 3.8 $\mu$m, are initially colorless and then change its color to dark brown with slightly thickening. The growth of aerial hyphae is vigorous and blastoconidium is formed from the side of the aerial hyphae. The vegetative hyphae and the aerial hyphae are fragmented to form thallic-arthric conidium. The thallic-arthric conidium is in the cylindrical or barrel form, has the size of 3.6 to 25 $\mu$m×2.2 to 4.3 $\mu$m. It is initially colorless and changes to pale brown. The blastoconidium is singular or a chain of three to four thereof. The conidium is in the slender elliptical form and has the size of 3.4 to 7.5 $\mu$m×1.9 to 4.1 $\mu$m (6.5±1.2 $\mu$m×3.8±0.6 $\mu$m on the average). It is initially colorless and then changes to olive-dark brown.

Morphological properties of this strain (MCI3369) are in well agreement with those of a standard strain of the parent strain *Trichosporonoides megachiliensis* CBS567.85. Thus, this strain was identified as *Trichosporonoides megachiliensis*.

MCI3371:

When cultivated at 24° C. on PDA medium, the color of the colony of strain MCI3369 is white to yellow white initially, then changes to dull yellow after one-week culture, and to black brown after further cultivating. The strain rapidly grows and proliferates by budding like yeasts. Daughter cells are initially thin film and color olive-dark brown. Thereafter, they thicken and darken. Vegetative hyphae grow concurrently with yeast-like budding. The vegetative hyphae have septum and branch. The width of the hyphae ranges from 2 to 4.5 m and their color is colorless initially to change to dark brown. The hyphae are fragmented to form thallic-arthric conidium. Blastoconidium is formed at the side or tip of the hyphae. The thallic-arthric conidium is in the cylindrical or barrel-like form, has the size of 6 to 35 $\mu$m×2.5 to 5.0 $\mu$m. It is initially colorless and changes to dark brown. The blastoconidium is singular or a chain of two to three thereof. The conidium is in the egg-like to elliptical or semispherical form and has the size of 4.7 to 9.4 $\mu$m×3.1 to 5.6 $\mu$m (6.8±1.3 $\mu$m×4.5±0.6 $\mu$m on the average). It is initially colorless and then changes to olive-dark brown.

This strain (MCI3371) has dimorphism: thallic-arthric conidium; and blastoconidium. The latter is characteristically formed directed to the tip and is not formed synchronously. Based on these characteristics, genus of this strain was searched in accordance with monograph of De Hoog & Hermanides-Nijhof (1977) and, as a result, it was found that this strain belongs to the genus Moniliella. According to De Hoog (1979) "The Black yeasts, II: Moniliella and Allied Genera" Studies in Mycology No. 19, 1–90, three species and two variants, *Moniliella suaveolens* var. *suaveolens*, *Moniliella suaveolens* var. *niger, Moniliella acetoabutens*, and *Moniliella pollinis* are known to belong to the genus Moniliella. These species and variants are classified based on mainly morphological characteristics of thallic-arthric conidium or blastoconidium. As a result of precise examination of morphological characteristics of this strain, it was in well agreement with the description of *Moniliella pollinis*. Therefore, this strain was identified as *Moniliella pollinis*.

MCI3437:

Strain MCI3437 shows initially white to yellow white, yellow dark brown after one-week culture, and dark yellow brown after more than two-week culture when cultivated at 24° C. on LCA. The growth rate is moderate. This strain proliferates by yeast-like budding. Daughter cells are initially thin film showing olive-dark brown, then thicken with turning to black brown, and proliferate by multilateral budding once to three or four times. Submerged hyphae grow concurrently with yeast-like budding. The submerged hyphae have septum and branch. Their width ranges from 2 to 4.5 $\mu$m and their color is initially colorless and then dark brown. The hyphae are fragmented to form thallic-arthric conidium. Alternatively, blastoconidium is formed from the side or tip of the hyphae. The thallic-arthric conidium has a cylindrical or barrel-like shape, variable length, and the width of from 2.5 to 5.0 $\mu$m. It is initially colorless and turns to dark brown. The blastoconidium is formed from the side and tip of the submerged hyphae and singular or a chain of two or three thereof. It has a hemisphere to elliptical form, the size of from 4.3 to 9.2×3.8 to 6.5 $\mu$m, colors dark brown, and thickens. It does not grow at 37° C.

This strain (MCI3437) has dimorphism: thallic-arthric conidium; and blastoconidium. The latter is characteristically formed directed to the tip and is not formed synchronously. Based on these characteristics, genus and species of this strain was compared with the parent strain of *Trichosporonoides nigrescens* and searched in accordance with monograph of G. S. de Hoog (1979) and the original description of A. D. Hocking & J. I Pitt (1981). As a result, the characteristics of this strain were in well agreement with those of *Trichosporonoides nigrescens*. Therefore, this strain was identified as *T. nigrescens*.

MCI3440:

Strain MCI3440 shows initially white to yellow white, brown after one-week culture, and dark yellow brown after more than two-week culture when cultivated at 24° C. on LCA. It grows rapidly and proliferates by yeast-like budding. Daughter cells are colorless and proliferate by multilateral budding once to three or four times. Submerged hyphae and aerial hyphae grow concurrently with yeast-like budding. The submerged hyphae and aerial hyphae have septum and branch. They have the width ranging from 2 to 4.5 $\mu$m and are colorless. The hyphae are fragmented to form thallic-arthric conidium. Alternatively, blastoconidium is formed from the side or tip of the hyphae. No vesicle is formed on LCA and PDA. The thallic-arthric conidium has a cylindrical or barrel-like shape, variable length, and the width of from 2.5 to 5.0 $\mu$m. It is colorless. The blastoconidium is formed from the side and tip of the submerged hyphae and singular or a chain of two or three thereof. It has an elliptical form, the size of from 4.7 to 8.1×2.5 to 3.4 $\mu$m, is colorless, and grows at 37° C.

This strain (MCI3440) has dimorphism: thallic-arthric conidium; and blastoconidium. The latter is characteristically formed directed to the tip of the submerged and aerial hyphae. It does not form Oedocephalis-type vesicle. According to the original description of Haskins & Spencer (1966), *Trichosporonoides oedocephalis* is mainly distinguished from other species (*T. spathulata, T. nigrescens, T. madida*, and *T. megachiliensis*) in the property to form vesicle. This variant (MCI3440) is different in this point from *T. oedocephalis*. As a result of comparing this strain with the parent strain of *T. oedocephalis* and searching genus and species of this strain in accordance with monograph of G. S. de Hoog (1979) and the original description of R. H. Haskins & J. F. T. Spencer (1966), its morphological properties were in well agreement with those of the parent strain of *T. oedocephalis*. Therefore, this strain was identified as *T. oedocephalis*.

MCI3554:

1) morphological properties

Colonies of strain MCI3554 show initially white to yellow white, yellow dark brown after one-week culture, and dark yellow brown after more than two-week culture when cultivated at 24° C. on PDA. The growth rate is moderate. This strain proliferates by yeast-like budding. Daughter cells are initially colorless, then thicken with turning to pale brown, to have the elliptical, egg-like or semispherical form and the size of 3.8 to 6.3 $\mu$m×3.0 to 5.0 $\mu$m. They proliferate by multilateral budding once to three or four times. Submerged hyphae and aerial hyphae grow concurrently with yeast-like budding. The submerged hyphae and aerial hyphae have the width ranging from 2.2 to 3.5 $\mu$m and have septum with branching. Their color is initially colorless and then becomes dark brown. The hyphae are fragmented to form thallic-arthric conidium. Alternatively, blastoconidium is formed from the side or tip of the hyphae. The thallic-arthric conidium has a cylindrical or barrel-like shape, variable length, and the width of from 9.4 to 18.8 $\mu$m×3.1× 4.1 $\mu$m. It is initially colorless and turns to dark brown. The blastoconidium is formed from the side and tip of the submerged hyphae and singular or a chain of two or three thereof. It has a hemisphere to elliptical form, the size of from 5.9 to 10.9×3.8 to 5.9 $\mu$m. It is initially colorless and then becomes dark brown with thickening.

2) Physiological properties

Growth temperature: 9° to 37° C. (cultivated on PDA for 10 days).

Optimal growth temperature: 27° to 30° C.

Growth pH: 4 to 9 (cultivated in LCA liquid medium for 10 days).

Optimal growth pH: 5 to 6

Utilization of carbon sources: shown in Table 1.

Fermentability of carbohydrate: shown in Table 2.

Utilization of nitrogen sources: shown in Table 3.

3) Taxonomical analysis

This strain (MCI3554) is characterized in that 1) it has yeast-like budding (daughter) cells, 2) it shows dimorphism: thallic-arthric conidium; and blastoconidium, and 3) the blastoconidium is characteristically formed directed to the tip and is not formed synchronously. Based on these characteristics, genus and species of this strain was searched with reference to the table of search in monograph of G. S. de Hoog (1979), "The Black Yeasts, II, Moniliella and Allied Genera, Studies in Mycology No. 19,1–36" and the description of species belonging to the genus Moniliella in G. S. de Hoog & D. Gueho (1984), "Deoxyribonucleic Acid Base Composition and Taxonomy of Moniliella and Allied Genera, Antonle van Leeuwenhook, 135–141". As a result, the characteristics of this strain were in well agreement with those of *Moniliella pollinis*. Further, when compared with the type strain (CBS 461.67) of *Moniliella pollinis*, it matches well its characteristics. Therefore, this strain was identified as *Moniliella pollinis*.

MCI3555:

1) Morphological properties

Strain MCI3555 is a mutant derived from *Moniliella pollinis* MCI3554. Colonies of strain MCI3555 show initially white to yellow white, yellow dark brown after one-week culture, and dark yellow-brown after more than two-week culture when cultivated at 24° C. on PDA. The growth rate is moderate. This strain proliferates by yeast-like budding. Daughter cells are initially colorless, then thicken with turning to pale brown, to have the elliptical, egg-like or semispherical form and the size of 4.0 to 7.8 $\mu$m×3.5 to 6.2 $\mu$m. They proliferate by multilateral budding once to three or four times. Submerged hyphae and aerial hyphae grow concurrently with yeast-like budding. The submerged hyphae and aerial hyphae have the width ranging from 1.3 to 4.1 $\mu$m and have septum with branching. Their color is initially colorless and then becomes dark brown. The hyphae are fragmented to form thallic-arthric conidium. Alternatively, blastoconidium is formed from the side or tip of the hyphae. The thallic-arthric conidium has a cylindrical or barrel-like shape, variable length, and the width of from 13.4 to 32.8 $\mu$m×2.5×4.1 $\mu$m. It is initially colorless and turns to dark brown. The blastoconidium is formed from the side and tip of the submerged hyphae and singular or a chain of two or three thereof. It has a hemisphere to elliptical form, the size of from 5.0 to 9.4×4.4 to 6.3 $\mu$m. It is initially colorless and then becomes dark brown with thickening.

2) Physiological properties

Growth temperature: 9° to 37° C. (cultivated on PDA for 10 days).

Optimal growth temperature: 27° to 30° C.

Growth pH: 4 to 9 (cultivated in LCA liquid medium for 10 days).

Optimal growth pH: 5 to 6

Utilization of carbon sources: shown in Table 1.

Fermentability of carbohydrate: shown in Table 2.

Utilization of nitrogen sources: shown in Table 3.

3) Taxonomical analysis

This strain (MCI3555) is characterized in that 1) it has yeast-like budding (daughter) cells, 2) it shows dimorphism: thallic-arthric conidium; and blastoconidium, and 3) the blastoconidium is characteristically formed directed to the tip and is not formed synchronously. Based on these characteristics, genus and species of this strain was searched with reference to the table of search in monograph of G. S. de Hoog (1979), "The Black Yeasts, II: Moniliella and Allied Genera, Studies in Mycology No. 19,1–36" and the description of species belonging to the genus Moniliella in G. S. de Hoog & D. Gueho (1984), "Deoxyribonucleic Acid Base Composition and Taxonomy of Moniliella and Allied Genera, Antonle van Leeuwenhook, 135–141". As a result, the characteristics of this strain were in well agreement with those of *Moniliella pollinis*. Further, when compared with the type strain (CBS 461.67) of *Moniliella pollinis*, it matches well its characteristics. Therefore, this strain was identified as *Moniliella pollinis*.

TABLE 1

| | Utilization of Carbon Sources | | |
|---|---|---|---|
| No. | Carbon Source | MCI3554 | MCI3555 |
| 1 | D-glucose | + | + |
| 2 | D-galactose | V | − |
| 3 | L-sorbose | ± | − |
| 4 | D-glucosamine | − | − |
| 5 | D-ribose | V | ± |
| 6 | D-xylose | ± | − |
| 7 | L-arabinose | ± | ± |
| 8 | D-arabinose | − | − |
| 9 | L-rhamnose | − | − |
| 10 | sucrose | + | + |

TABLE 1-continued

Utilization of Carbon Sources

| No. | Carbon Source | MCI3554 | MCI3555 |
|---|---|---|---|
| 11 | maltose | + | + |
| 12 | α,α-trehalose | – | – |
| 13 | methyl α-D-glucoside | – | – |
| 14 | cellobiose | + | + |
| 15 | salicin | – | – |
| 16 | arbutin | + | + |
| 17 | melibiose | – | – |
| 18 | lactose | – | – |
| 19 | raffinose | – | – |
| 20 | melezitose | – | – |
| 21 | inulin | – | – |
| 22 | Soluble starch | – | – |
| 23 | glycerol | + | + |
| 24 | meso-erythritol | + | + |
| 25 | ribitol | – | – |
| 26 | xylitol | + | ± |
| 27 | L-arabinitol | – | – |
| 28 | D-glucitol | – | – |
| 29 | D-mannitol | + | + |
| 30 | galactitol | – | – |
| 31 | myo-inositol | – | – |
| 32 | glucono-δ-lactone | ± | ± |
| 33 | D-gluconic acid | – | – |
| 34 | D-glucuronic acid | – | – |
| 35 | D-galacturonic acid | – | – |
| 36 | DL-lactic acid | – | – |
| 37 | succinic acid | ± | ± |
| 38 | citric acid | ± | ± |
| 39 | methanol | – | – |
| 40 | ethanol | + | + |

+: utilizable. : cannot say which, V: undetermined, and –: not utilize.

TABLE 2

Fermentability of Carbohydrates

| No. | Carbohydrate | MCI3554 | MCI3555 |
|---|---|---|---|
| 1 | D-glucose | + | + |
| 2 | D-galactose | – | – |
| 3 | maltose | + | + |
| 4 | sucrose | + | + |
| 5 | lactose | – | – |
| 6 | raffinose | – | – |

+: fermentable, –: not ferment

TABLE 3

Utilization of Nitrogen Sources

| Nitrogen source | MCI3554 | MCI3555 |
|---|---|---|
| ammonium sulfate | + | + |
| potassium nitrate | + | + |
| L-lysine | + | + |
| cadaverine | + | + |

+: utilizable, –: not utilize

The main carbon sources used in the culture medium for cultivating these yeast strains are not particularly restricted as long as they are fermentable carbohydrate. Preferably, fermentable carbohydrate such as glucose, fructose and glycerol can be used. Glucose is particularly preferred. These fermentable carbohydrates can be used alone or in combination thereof. Though their concentrations are not particularly restricted, it is beneficial to use a concentration as high as possible within the range that does not inhibit the production of erythritol. The concentration ranges preferably from 20 to 50% (w/v), more preferably from 35 to 40% (w/v).

The nitrogen sources are preferably composed of ammonium sulfate in an amount of 50 to 85% of the total nitrogen sources in terms of nitrogen atom and various organic or inorganic nitrogen-containing compounds such as ammonium salt other than ammonium sulfate, peptone, yeast extract, corn steep liquor, and the like in an amount of the rest (15 to 50%) of the total nitrogen sources. The rest of the nitrogen sources other than ammonium sulfate is preferably corn steep liquor. The use of ammonium sulfate in an amount of less than 50% is unfavorable since glycerol may be formed as a by-product, erythritol obtained colors dark brown, or a large amount of salts contaminates. On the other hand, the use of ammonium sulfate in an amount of more than 85% is also unfavorable since the yield of erythritol is reduced. Examples of the inorganic salts include various phosphoric salts, sulfuric salts, salts with metal such as magnesium, potassium, manganese, iron, zinc, or the like. If necessary, factors capable of promoting growth of the yeast strains may be added. Examples thereof include vitamins, nucleotides, amino acids, and the like. It is desirable to add an appropriate amount of a commercially available antifoam agent in order to prevent bubbling during cultivation.

The culture medium is adjusted to have a pH of 3 to 7, preferably 3 to 4.5, more preferably 3.5 to 4.0, at the initial stage of fermentation. The temperature is adjusted to 25° to 40° C., preferably 30° to 37° C., during cultivation.

To begin cultivating, the microbial cells may be directly inoculated from slant to the culture medium. Preferably, the cells are cultivated in a liquid medium for one to four days and the resulting culture is inoculated into the culture medium. The culture is carried out under aerobic conditions by stirring under aeration or shaking. The culture is preferably continued until the main carbon source is exhausted, generally for three to six days. The amount of erythritol produced can be determined by gas chromatography, high performance liquid chromatography, or the like.

Erythritol thus accumulated in the culture medium can be isolated and purified from the culture medium by the usual methods. Specifically, erythritol can be isolated and purified by removing the solid matters including the microbial cells by centrifugation, filtration, or the like, subjecting the resulting liquid to desalting and decolorization by treatment with ion exchange resin or activated carbon, and carrying out recrystallization from the resulting solution.

According to the method of the present invention, erythritol can be produced efficiently in high yield using safe and inexpensive nitrogen sources which are admitted as food additives.

DETAILED DESCRIPTION OF THE PREFERRED EMBODIMENTS

The following Examples will illustrate the present invention in more detail, but are not to be construed to limit the scope of the invention as long as they are fallen within the subject matter of the invention.

(Composition of culture medium)

TABLE 4

| Glucose | 40% |
|---|---|
| Corn steep liquor (Ohji Corn Starch) | 1.5% |
| Ammonium sulfate | 0.886% |
| Potassium dihydrogen phosphate | 0.1% |

TABLE 4-continued

| | |
|---|---|
| Zinc sulfate | 0.005% |
| Vitamin B$_1$ | 0.005% |
| Antifoam agent | 0.05% |

In Table 4 above, the ratio of ammonium sulfate to corn steep liquor as the nitrogen source is about 4:1 in terms of the nitrogen ratio (the nitrogen content of corn steep liquor: 3% on the average).

EXAMPLES 1 TO 3

To a cotton-wool-plugged 500-ml conical flask was added 100 ml of a liquid medium containing 30% (w/v) of glucose and 1% of yeast extract (Asahi Breweries) followed by sterilization at 120° C. for 20 minutes. The flask was respectively inoculated with slants of MCI3437, MCI3440, and MCI3555, which were prepared by the conventional method, and cultivated at 30° C. for 3 days with shaking (seed culture). Ten ml of the seed culture was used to inoculate a 1-liter fermentor containing 500 ml of the culture medium shown in Table 4 above and cultivated at 35° C., 0.5 vvm of aeration, and 800 rpm for 4 days. The pH of the medium at the time of inoculation was 3.9 to 4.0 and the pH was maintained at 3.5 to 3.7 by adding a 35% sodium hydroxide aqueous solution during cultivation. The concentrations of erythritol and glycerol in the culture medium were measured by high performance liquid chromatography and the degree of coloring of the supernatant of the broth after completion of the cultivation was determined by measuring absorbance at 420 nm by a spectrophotometer.

The results of the amount of erythritol produced, the amount of glycerol produced, and the degree of coloring of the culture medium of each strain were as follows.

TABLE 5

| Example No. | Strain | Amount of erythritol | Amount of glycerol | Amount of coloring (A$_{420}$) |
|---|---|---|---|---|
| 1 | MCI3437 | 150.9 g/L | 66.6 g/L | 0.412 |
| 2 | MCI3440 | 124.5 g/L | 3.0 g/L | 0.552 |
| 3 | MCI3555 | 170.3 g/L | 4.5 g/L | 0.673 |

EXAMPLE 4

To a cotton-wool-plugged 500-ml conical flask was added 100 ml of a liquid medium containing 30% (w/v) of glucose and 1% of yeast extract (Asahi Breweries) followed by sterilization at 120° C. for 20 minutes. The flask was inoculated with a loopful of slant of MCI3369, which was prepared by the conventional method, and cultivated at 35° C. for 3 days with shaking. (The resulting seed culture is referred to as "seed culture A".) To a cotton-wool-plugged 500-ml conical flask was added 100 ml of a liquid medium containing 30% (w/v) of glucose and 1% of yeast extract (Asahi Breweries) followed by sterilization at 120° C. for 20 minutes. The flask was inoculated with 2 ml of the above seed culture A and cultivated at 35° C. for 3 days with shaking. (The resulting seed culture is referred to as "seed culture B".) Three hundred ml of the above seed culture B was used to inoculate a 30-liter fermentor containing 15 liter of the culture medium shown in Table 4 above and cultivated at 35° C., 0.5 vvm of aeration, internal pressure of 0.5 kg/cm$^2$G, and 350 rpm for 4 days. The pH of the medium at the time of inoculation was 3.9 to 4.0 and the pH was maintained at 3.5 to 3.7 by adding a 35% sodium hydroxide aqueous solution during cultivation. The concentrations of erythritol and glycerol in the culture medium were measured by high performance liquid chromatography. As a result, the ratio of yield of erythritol to glucose was 48.2%, while the ratio of yield of glycerol to glucose was 1.1%. The degree of coloring of the supernatant of the broth after completion of the cultivation was 0.367 at 420 nm.

EXAMPLE 5

Three hundred ml of the above seed culture A was used to inoculate a 30-liter fermentor containing 15 liter of the liquid medium containing 30% (w/v) of glucose, 3.7% of corn steep liquor (Ohji Corn Starch), and 0.1% of an antifoam agent and cultivated at 35° C., 0.5 vvm of aeration, internal pressure of 0.5 kg/cm$^2$G, and 330 rpm for 3 days. (The resulting seed culture is referred to as "seed culture C".) Three hundred ml of the above seed culture C was used to inoculate a 30-liter fermentor containing 15 liter of the culture medium shown in Table 4 above and cultivated at 35° C., 0.5 vvm of aeration, internal pressure of 0.5 kg/cm$^2$G, and 330 rpm for 4 days. The pH of the medium at the time of inoculation was 3.9 to 4.0 and the pH was maintained at 3.5 to 3.7 by adding a 35% sodium hydroxide aqueous solution during cultivation. The concentration of erythritol in the culture medium was measured by high performance liquid chromatography. As a result, the ratio of yield of erythritol to glucose was 47.2%, while the ratio of yield of glycerol to glucose was 0.9%. The degree of coloring of the supernatant of the broth after completion of the cultivation was 0.395 at 420 nm.

EXAMPLE 6

Erythritol was produced in the same manner as in Example 4 except for using MCI3371. The ratio of yield of erythritol to glucose was 48.0%, while the ratio of yield of glycerol to glucose was 4.5%. The degree of coloring of the supernatant of the broth after completion of the cultivation was 0.353 at 420 nm.

EXAMPLE 7

To a cotton-wool-plugged 500-ml conical flask was added 100 ml of a liquid medium containing 30% (w/v) of glucose and 1% of yeast extract (Asahi Breweries) followed by sterilization at 120° C. for 20 minutes. The flask was inoculated with strain ATCC 8661, which was cultivated on a slant by the conventional method, and cultivated at 30° C. for 3 days with shaking (seed culture). One hundred ml of the seed culture was used to inoculate a 5-liter fermentor containing 2.5 liter of the culture medium shown in Table 4 above and cultivated at 30° C., 1 vvm of aeration, 900 rpm, and internal pressure of 0.5 kg/cm$^2$G for 5 days. The pH of the medium at the time of inoculation was 3.9 to 4.0 and the pH was maintained at 3.5 to 3.7 by adding a 35% sodium hydroxide aqueous solution during cultivation. The concentrations of erythritol and glycerol in the culture medium were measured by high performance liquid chromatography. As a result, the ratio of yield of erythritol to glucose was 43.9%. The degree of coloring of the supernatant of the broth after completion of the cultivation was 0.365 at 420 nm.

EXAMPLES 8 TO 12

To a cotton-wool-plugged 500-ml conical flask was added 100 ml of a liquid medium containing 30% (w/v) of glucose and 1% of yeast extract (Asahi Breweries) followed by sterilization at 120° C. for 20 minutes. The flask was inoculated with strain MCI3555, which was cultivated on a slant by the conventional method, and cultivated at 30° C. for 3 days with shaking (seed culture). Ten ml of the seed culture was used to inoculate a 1-liter fermentor containing 500 ml of the culture medium having the same composition as shown in Table 4 above except for changing the ratio of corn steep liquor and ammonium sulfate as shown in Table 6 and cultivated at 35° C., 0.5 vvm of aeration, and 800 rpm, for 4 days. The pH of the medium at the time of inoculation was 3.9 to 4.0 and the pH was maintained at 3.5 to 3.7 by adding a 35% sodium hydroxide aqueous solution during cultivation.

TABLE 6

| Example No. | Amount of corn steep liquor | Amount of Ammonium sulfate |
| --- | --- | --- |
| 8 | 3.0264% | 0.5044% |
| 9 | 2.5220% | 0.6305% |
| 10 | 1.2610% | 0.94575% |
| 11 | 0.7566% | 1.07185% |
| 12 | 0.5044% | 1.1349% |

The results of the amount of erythritol produced, the amount of glycerol produced, and the degree of coloring of the each culture medium were as follows.

TABLE 7

| Example No. | Amount of erythritol | Amount of glycerol | Degree of coloring ($A_{420}$) |
| --- | --- | --- | --- |
| 8 | 160.5 g/L | 10.2 g/L | 1.585 |
| 9 | 180.5 g/L | 6.7 g/L | 1.318 |
| 10 | 169.3 g/L | 4.8 g/L | 0.993 |
| 11 | 135.2 g/L | 27.0 g/L | 0.721 |
| 12 | 89.7 g/L | 45.0 g/L | 0.691 |

Comparative Example 1 to 3

Erythritol was produced in the same manner as in Examples 1 to 3 except for using the culture medium having the composition shown in Table 8 in place of the culture medium having the composition shown in Table 4.
(Composition of culture medium of Comparative Example)

TABLE 8

| Glucose | 40% |
| --- | --- |
| Corn steep liquor (Ohji Corn Starch) | 8% |
| Antifoam agent | 0.05% |

In Table 8, the nitrogen source used was only corn steep liquor and the nitrogen content of this composition is the same as in the composition shown in Table 4 in terms of nitrogen atom.

The results of the amount of erythritol produced, the amount of glycerol produced, and the degree of coloring of the broth supernatant of each strain were as follows.

TABLE 9

| Comparative Example No. | Strain | Amount of erythritol | Amount of glycerol | Degree of coloring ($A_{420}$) |
| --- | --- | --- | --- | --- |
| 1 | MCI3437 | 137.3 g/L | 76.2 g/L | 3.131 |
| 2 | MCI3440 | 109.3 g/L | 18.7 g/L | 2.707 |
| 3 | MCI3555 | 167.5 g/L | 14.5 g/L | 3.112 |

Comparative Example 4

Erythritol was produced in the same manner as in Example 4 except for using the culture medium having the composition shown in Table 8 in place of the culture medium having the composition shown in Table 4. As a result, the ratio of yield of erythritol to glucose was 39.8%, while the ratio of yield of glycerol to glucose was 19.5%.

Thus, the present invention provides improved yield of erythritol.

While the invention has been described in detail and with reference to specific embodiments thereof, it will be apparent to one skilled in the art that various changes and modifications can be made therein without departing from the spirit and scope thereof.

What is claimed is:

1. A method of producing erythritol comprising the steps of cultivating a yeast strain capable of producing erythritol from fermentable carbohydrate in a culture medium containing the fermentable carbohydrate as a main carbon source and recovering erythritol from the culture, wherein said culture medium contains ammonium sulfate as a main nitrogen source.

2. The method of producing erythritol according to claim 1, wherein an amount of ammonium sulfate ranges from 50 to 85% of the total nitrogen sources in the medium in terms of nitrogen atom.

3. The method of producing erythritol according to claim 2, wherein said medium further contains corn steep liquor as a nitrogen source, and an amount of ammonium sulfate ranges from 50 to 85% and an amount of corn steep liquor ranges from 15 to 50%, of the total nitrogen sources in the medium in terms of nitrogen atom.

4. The method of producing erythritol according to claim 1, wherein said yeast strain belongs to the genus Moniliella.

5. The method of producing erythritol according to claim 4, wherein said yeast strain is *Moniliella pollinis*.

6. The method of producing erythritol according to claim 1, wherein said yeast strain belongs to the genus Yarrowia.

7. The method of producing erythritol according to claim 6, wherein said yeast strain is *Yarrowia lipolytica*.

8. The method of producing erythritol according to claim 1, wherein said yeast strain belongs to the genus Trichosporonoides.

9. The method of producing erythritol according to claim 8, wherein said yeast strain is selected from the group consisting of *Trychosporonoides oedocephalis*, *Trychosporonoides nigrescens* and *Trychosporonoides megachiliensis*.

10. The method of producing erythritol according to claim 1, wherein said fermentable carbohydrate is selected from the group consisting of glucose, fructose and glycerol.

11. The method of producing erythritol according to claim 1, wherein the nitrogen source is contained in the medium in a concentration of from 0.1 to 5.0% (w/v).

12. The method of producing erythritol according to claim 1, wherein a pH of the culture medium is maintained at 3.0 to 7.0.

* * * * *